United States Patent [19]

Manning et al.

[11] Patent Number: 4,723,442

[45] Date of Patent: * Feb. 9, 1988

[54] HIGH-TEMPERATURE, HIGH-SHEAR CAPILLARY VISCOMETER

[75] Inventors: Robert E. Manning, Boalsburg; Wallis A. Lloyd, State College, both of Pa.

[73] Assignee: Cannon Instrument Company, State College, Pa.

[*] Notice: The portion of the term of this patent subsequent to Aug. 11, 2004 has been disclaimed.

[21] Appl. No.: 932,858

[22] Filed: Nov. 20, 1986

Related U.S. Application Data

[63] Continuation-in-part of Ser. No. 842,088, Mar. 18, 1986, Pat. No. 4,658,636.

[51] Int. Cl.[4] ............................................. G01N 11/06
[52] U.S. Cl. ......................................................... 73/55
[58] Field of Search ................................ 73/55, 861.05

[56] References Cited

U.S. PATENT DOCUMENTS

| | | | |
|---|---|---|---|
| 2,700,891 | 2/1955 | Shafer | 73/55 |
| 2,805,570 | 9/1957 | Cannon | 73/55 |
| 3,277,694 | 10/1966 | Cannon et al. | 73/55 |
| 3,435,665 | 4/1969 | Tzentis | 73/56 |
| 3,543,578 | 12/1970 | Sampson | 73/861.05 X |
| 4,274,279 | 6/1981 | Meister | 73/55 |
| 4,441,358 | 4/1984 | Osborne | 73/55 |

OTHER PUBLICATIONS

ASTM Specification D446.
ASTM Test Method D2171.
ASTM Special Technical Bulletin No. 111, (1951), (copy not enclosed).
S. J. Weeds, "The Kingsbury Tapered-Plug Viscometer for Determining Viscosity Variations Within Temperature and Rates of Shear".

*Primary Examiner*—Stewart J. Levy
*Assistant Examiner*—Joseph W. Roskos
*Attorney, Agent, or Firm*—Seidel, Gonda, Goldhammer & Abbott

[57] ABSTRACT

A high-temperature, high-shear viscometer includes a closed end tube having a chamber. A first inlet to the tube is for introducing pressurized gas therein. A second inlet to the tube is for introducing the liquid into the chamber and removing excess liquid from the chamber. A capillary tube is in communication with the chamber. An outlet for the liquid is in communication with the capillary tube. A timer is provided for measuring the efflux time of the liquid in the capillary tube. The timer is started by a device in communication with the first inlet. The timer is stopped by a device which senses the movement of the pressurized gas. The movement sensor includes a thermistor.

8 Claims, 5 Drawing Figures

HIGH-TEMPERATURE, HIGH-SHEAR CAPILLARY VISCOMETER

RELATED APPLICATION

This application is a continuation-in-part of copending U.S. patent application Ser. No. 842,088 filed Mar. 18, 1986, now U.S. Pat. No. 4,658,636, by co-inventors R. E. Manning and W. A. Lloyd, assigned to Cannon Instrument Co. and entitled "High-Temperature, High-Shear Capillary Viscometer".

BACKGROUND OF THE INVENTION

1. Field of the Invention

The present invention is directed to a new capillary viscometer for measuring the flow properties, especially viscosity, of liquids, such as engine oil, at high temperatures and high shear rates.

2. Description of the Prior Art

Many types of viscometers have been used for the measurement of flow properties of liquids. These include:
   a. Capillary viscometers; and
   b. Rotational viscometers.

Capillary viscometers include glass capillary kinematic viscometers (see ASTM specifications D446 and U.S. Pat. No. 2,805,570) which operate with a liquid flow induced by gravity and produce relatively low shear rates. Other capillary viscometers utilize vacuum or pressure to cause liquid flow (see ASTM test method D2171 and U.S. Pat. No. 3,277,694) and produce higher shear rates.

These capillary viscometers are not designed for high-temperature, high-shear operation. Thus, they are unsuitable for viscosity measurements at high-temperature and high-shear, as described herein.

U.S. Pat. Nos. 3,435,665 and 4,441,358 disclose capillary viscometers. U.S. Pat. No. 3,435,665 discloses a capillary tube directly connected to an manometer. An inert fluid forces a test fluid through the capillary tube. The moving test fluid causes the manometer fluid to fluctuate within the manometer tube. Two photoelectric cells are operatively connected to a timer. The photoelectric cells and timer measure the lapse time it takes the meniscus of the manometer fluid to travel between two points on the manometer tube. This capillary viscometer is not adapted for high-temperature, high-shear viscosity measurements. U.S. Pat. No. 4,441,358 discloses a capillary viscometer having at least two sets of piezo electric ultrasonic transducers mounted along a length of the capillary tube. The transducers monitor the movement of the test fluid meniscus as it travels between the transducers. The transducers initiate and terminate the timer. This viscometer does not disclose the present invention.

Rotational viscometers include the Stormer Viscometer which is used to produce low shear rates. The Kingsbury Tapered-Plug Viscometer (see ASTM Special Technical Bulletin No. 111 (1951), S. J. Weeds, "The Kingsbury Tapered-Plug Viscometer For Determining Viscosity Variations Within Temperature and Rates of Shear") and the Tapered Bearing Simulator (U.S. Pat. No. 4,274,279) are suitable for the measurement of engine oil lubricant flow properties at high temperatures (100° to 200° C.) and at high shear rates of $10^6 sec^{-1}$. These two high shear rotational viscometers are well suited for laboratory research purposes, but are complex in operation and require highly trained technicians and maintenance personnel for operation and repair.

There is a need for a relatively simple viscometer which overcomes the complexity of the tapered-rotational and rotational instruments, which has the relative simplicity of capillary viscometers, and that can be adapted to high-temperature high-shear operation.

SUMMARY OF THE INVENTION

The present invention is directed to a high-temperature, high-shear viscometer for a liquid. This viscometer utilizes a pressurized gas to force the liquid through the viscometer. The viscometer includes a closed ended tube defining, in part, a chamber. A first inlet is provided for introducing the pressurized gas into the tube. A second inlet is provided for introducing the liquid to the chamber and for removing excess fluid from the chamber. A capillary tube communicates with the chamber. An outlet for the liquid communicates with the capillary tube. A timer measures the time the liquid takes to move through the capillary tube. The timer is started by a means which communicates with the first inlet. The timer is stopped by a means which senses the movement of the pressurized gas after the liquid has exited the capillary tube. Additionally, the viscometer has a heater means for bringing the liquid to a test temperature.

The means for stopping the timer is herein described as including a thermistor. The thermistor is operatively associated with the timer.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
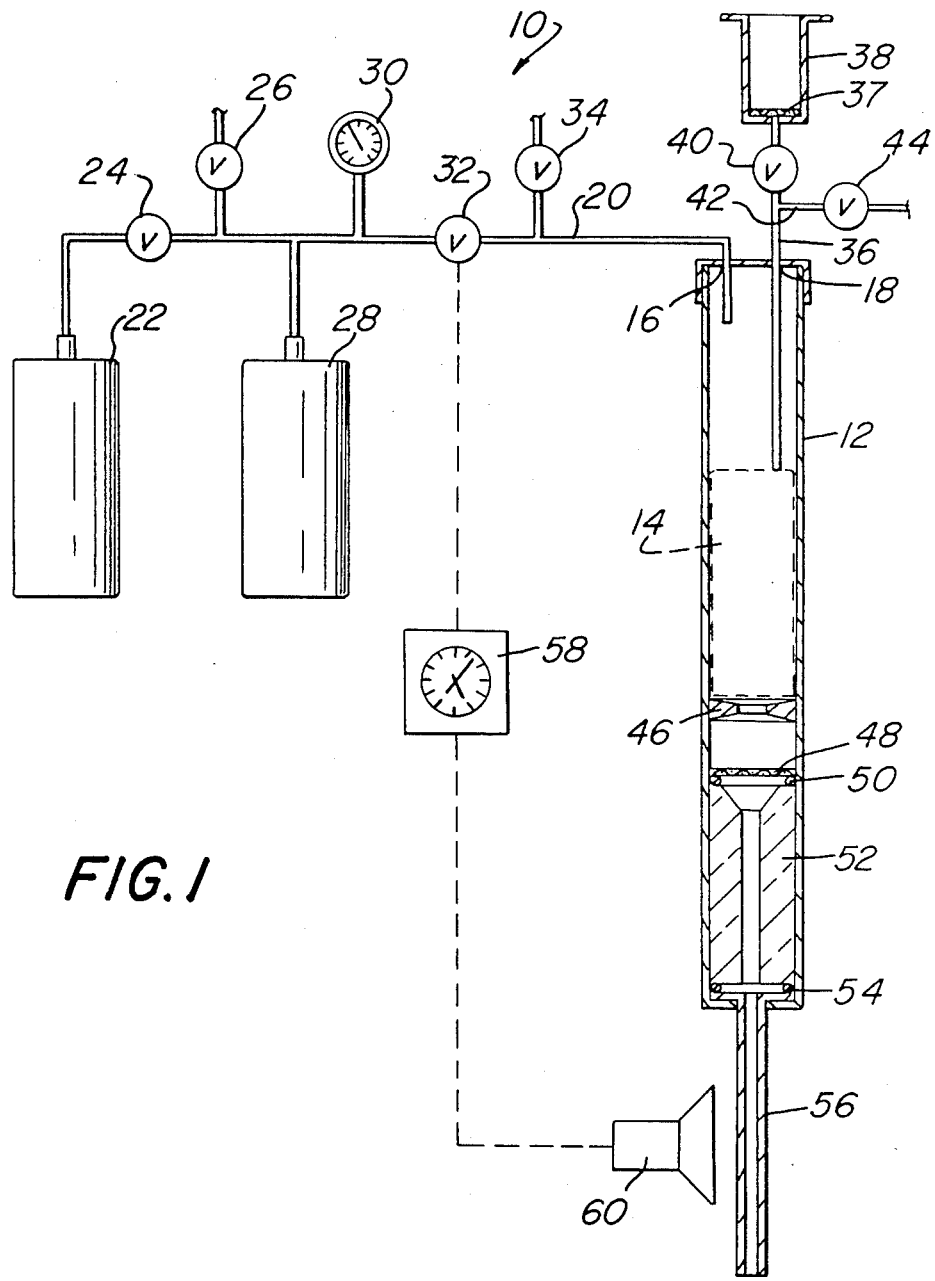
FIG. 1 is a schematic representation of a first embodiment of the present invention.

Referring to the figures, wherein like elements are designated by like numerals, there is shown in FIG. 1 a viscometer 10 made according to the present invention.

Viscometer 10 includes a closed ended tube 12 surrounded by constant temperature bath (not shown). The tube 12 is designed to withstand pressures ranging from about 50 to 1500 psig, although preferably the viscometer is operated between about 125–500 psig. The tube has an internal diameter of between about 5 to 30 mm. If the internal diameter is too large, heat flow through the tube wall will increase the time to bring the test liquid to thermal equilibrium and impede the drainage of the test liquid thereby reducing the uniformity of repeatability of the test. Tube 12 has an overall length of about 60–400 mm. If the length is too short, the efflux volume of the test sample may show a larger relative variation. If the length is too long, it is more difficult to achieve close temperature control. The preferred dimensions of tube 12 are 13 mm internal diameter and 220 mm in length.

Tube 12 is surrounded by a constant temperature bath. The bath may be any constant temperature bath which is capable of sustaining a temperature between about 100° C. to 200° C. to within ±0.1° C. or preferably 150° C.±0.1° C. Such baths generally include liquid baths and air baths. Preferably, the bath is an aluminum block having a hole therethrough. The tube 12 is held tightly within the hole. The block is maintained at a temperature using a conventional heater and thermostat. Any bath used should be well insulated to minimize heat loss. Optionally, a temperature sensor (not shown) may be included to indicate when the test sample has reached thermal equilibrium.

A narrow-bore capillary tube 52 is secured within the lower portion of tube 12. The capillary tube is preferably made of glass. The bore of the capillary tube is generally between about 0.10 to 0.30 mm in diameter and preferably is about 0.15 mm in diameter. The length of the bore is generally about 5 to 80 mm and preferably about 15 mm. The ratio of the length to diameter is generally about 50 to 500 and preferably about 100. The ends of the bore may be "square-cut" or have a smooth converging taper or may be a combination of square-cut and taper.

O-rings 50 and 54 are placed in contact with both the ends of capillary tube 52 and the inner wall of tube 12. The O-rings 50 and 54 are preferably made of an elastomeric material. The O-rings 50 and 54 act as shock absorbers to reduce the likelihood of damage to the capillary tube and as sealing gaskets to prevent test liquids and pressurized gas from passing around the capillary tube 52.

A fine mesh screen 48, between 100-1000 mesh and preferably about 400 mesh, is securable within tube 12 above O-ring 50. Screen 48 prevents particles in the test fluid from clogging the bore of the capillary tube 52 and distorting the resulting viscosity measurement. Screen 48 is optional, if the test fluid is free of any particles.

The upper end of the tube 12 has a first inlet 16 and a second inlet 18. The first inlet 16 is connected to a pressurized inert gas line 20. A source of pressurized inert gas 22 is connected to a terminal end of line 20. A throttle/shut-off valve 24 is fixed on line 20 and is provided for controlling the release of pressurized gas from source 22. A ballast tank 28 is connected to line 20 between gas source 22 and tube 12. Ballast tank 28 allows pressurized gas from source 22 to be set at a predetermined test pressure which is measured by a pressure gauge or pressure transducer 30 affixed to line 20. A bleed valve 26 is affixed to line 20 between valve 24 and tank 28. Bleed valve 26 allows pressurized gas in the tank 28 to be controlled to a predetermined value and is vented to the atmosphere. Valves 24 and 26 are throttle valves and may include an electric (solenoid) valve.

A shut-off valve 32 is affixed to line 20 between gauge 30 and tube 12. The valve 32 isolates the pressurized gas from tube 12 while the liquid is prepared for the viscosity test. Another function of valve 32 will be explained below. A vent valve 34 is affixed to line 20 between valve 32 and tube 12 and when opened is vented to the atmosphere. Its use will be explained below. Valve 32 and 34 are preferably not throttle valves as rapid application of pressurized gas from the ballast tank 28 to tube 12 and rapid release of gas pressure to atmosphere following the efflux-time (lapse time) measurement, is desired. Valves 32 and 34 may be manual toggle valves or combined into a "3-way" toggle valve, or electric two- or three-way valves.

A second line 36 passes through the second inlet 18 into tube 12 and extends above the upper end of tube 12. A graduated fill tube 38 (such as the barrel of a syringe) is affixed to the uppermost end of line 36. The fill tube 38 is for introducing an excess of the test liquid into tube 12 via line 36. A fine mesh screen 37, generally 100–1000 mesh and preferably 400 mesh, is placed in the lowermost end of fill tube 38. Screen 37 prevents particles in the test fluid from passing into tube 12. Screen 37 is optional, if the test fluid is free of any particles. A shut-off valve 40 is located below fill tube 38 and isolates the fill tube 38 from tube 12. Valve 40 is a throttle valve and may be either a manual or electric (solenoid) valve. A vacuum line 42 and a vacuum shut-off valve 44 are affixed to line 36 between valve 40 and tube 12. The use of the vacuum line 42 and shut-off valve 44 will be explained below.

A safety orifice 46 is located within and secured to tube 12. The safety orifice is located a distance below the free end of line 36 and above fine mesh screen 48. It is provided to limit gas flow rates, if tube 12 is pressurized without capillary 52 in position. The diameter of the orifice is 0.2 to 2 mm preferably 0.8 mm.

A chamber 14 is defined by the lower free end of line 36, safety orifice 46 and the inside walls of tube 12. The test liquid introduced into tube 12 via line 36 fills chamber 14 and may be in excess. The test liquid is heated to test temperature in chamber 14 and may expand beyond chamber 14. Prior to the start of the viscocity test, test liquid in excess of chamber 14 is removed in a manner described below. The distance between the lower free end of line 36 and safety orifice 46 is generally any fixed distance which will insure a repeatable constant volume of the test liquid and is preferably about 66 mm.

An outlet 56 is located at the lowermost end of tube 12 and communicates with capillary tube 52. Outlet 56 allows test liquid to exit tube 12 after being discharged through capillary tube 52.

A timer 58 is provided for measuring the efflux-time (lapse time) of the test liquid passing through the capillary tube 52. Timer 58 is operatively connected to valve 32. Valve 32 is provided with means for initiating timer 58 when it is opened to allow pressurized gas into tube 12, such as are known to those skilled in the art. Timer 58 is any timer capable of being started and stopped from an externally generated signal. Such a timer is, for example, the DCI Model 812'-31 Stopclock manufactured by DCI of Olathe, KS.

An acoustic pick up 60 is operatively connected to timer 58 and is located adjacent capillary tube 52 and outlet 56. The acoustic pick up 60 stops the timer 58 when it hears the "hiss" made by the movement of the pressurized gas exiting the capillary tube 52 and/or the outlet 56. Positioning of the acoustic pick up 60 adjacent capillary tube 52 and/or outlet 56 is not critical as the "hiss" is typically loud enough to be heard at a distance from the viscometer. The acoustic pick up 60 is, for example, a Digi-Key Part No. P9932 microphone element sold by Digi-Key of Thief River Falls, NJ.

The acoustic pick up 60 is serially connected (not shown) via two amplifiers, for example, LM 38 6N Audio amplifier manufactured by National Semiconductor of Santa Clara, CA, and an opto-isolator, for example, GEH1123 opto-isolator, manufactured by General Electric of Schenectady, NY. This circuitry is non-limiting as those skilled in the art will recognize that other circuitry can perform the same function.

Figure 2:
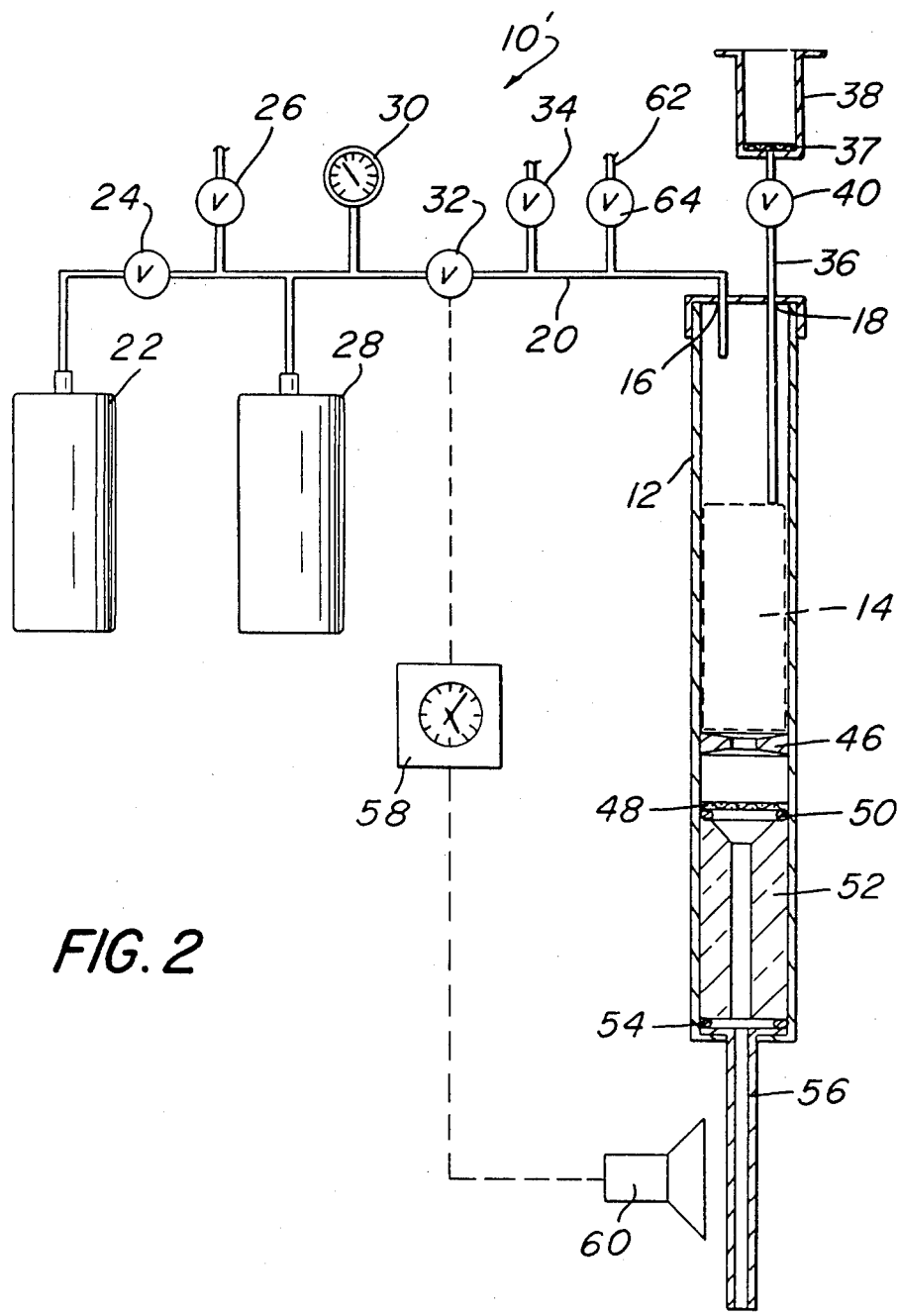
FIG. 2 is a schematic representation of a second embodiment.

Referring to FIG. 2, a second embodiment of the present invention 10' is shown. Elements which are the same as those described in FIG. 1 have the same numerical notation. Only those portions of the second embodiment which differ from the first embodiment are discussed.

The second embodiment is identical to the first embodiment, except for the following. The first inlet 16 includes a line 62 and a valve 64. Valve 64 is affixed to line 62. Line 62 is located on line 20 between valve 32 and tube 12. Valves 42 (first embodiment) and 64 are manual needle valves adjusted for only a very low flow, or can be used in combination with an electric valve. Line 62 is connected to a source of low pressure inert gas. The use of the low pressure gas is described below.

Figure 3:
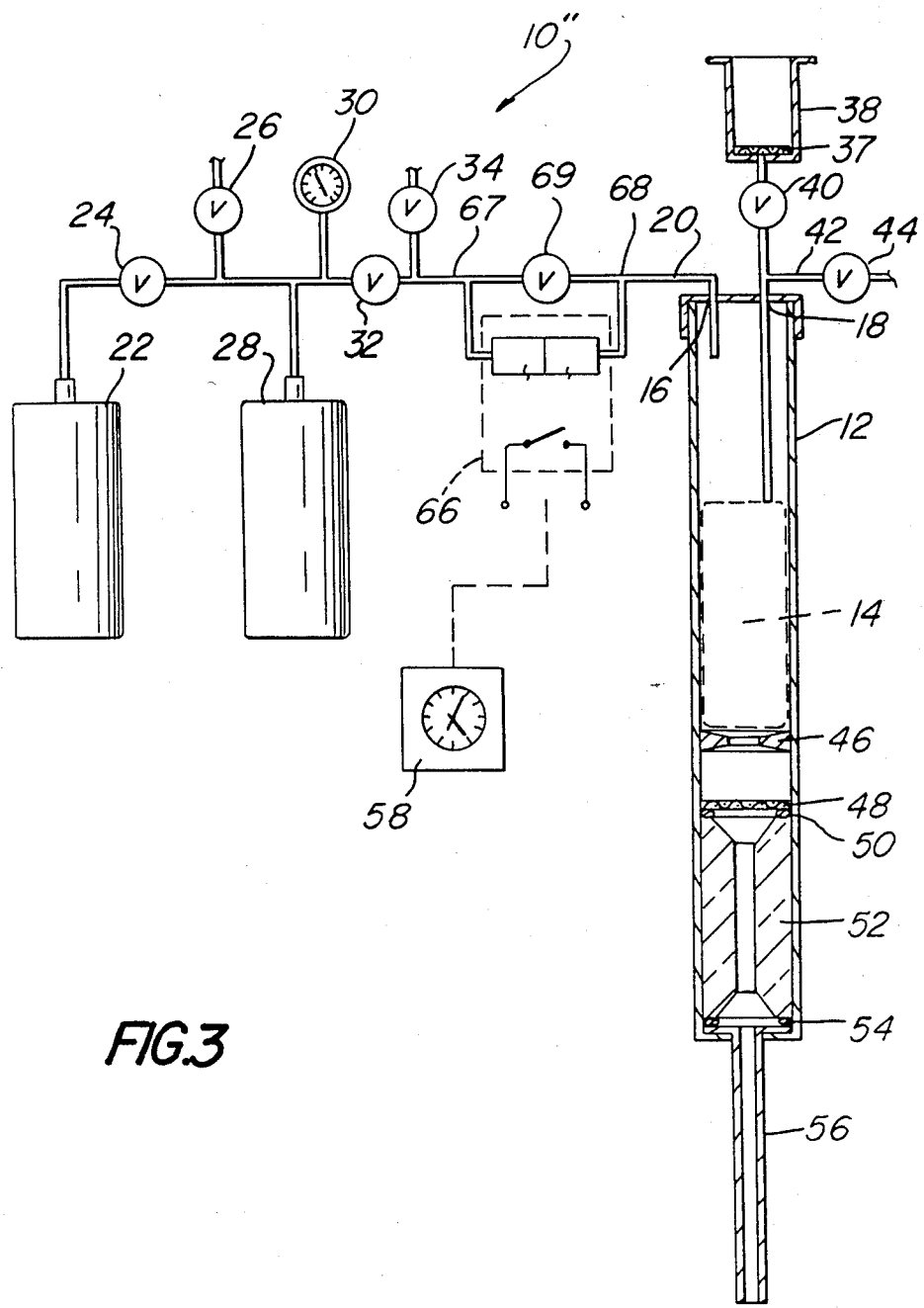
FIG. 3 is a schematic representation of a third embodiment.

Referring to FIG. 3, a third embodiment of the present invention 10'' is shown. The third embodiment is directed to a different type of gas movement sensor. The other portions of the viscometer can be the same as shown in either FIGS. 1 or 2. Elements common to FIGS. 1 and 2 are denoted with like numerals.

A sensitive pressure differential switch 66 is placed in line 20 between valve 32 and tube 12. The switch 66 senses the low resistance to gas flow between points 67 and 68. A throttle valve 69 may be inserted between 67 and 68 to allow adjustment of the resistance. The pressure differential switch, which is well-known in the art, is capable of detecting the movement of the pressurized gas in line 20. Its use is explained below. Pressure differential switch 66 is operably connected to timer 58 in any manner well known to those skilled in the art.

Figures 4, 5:
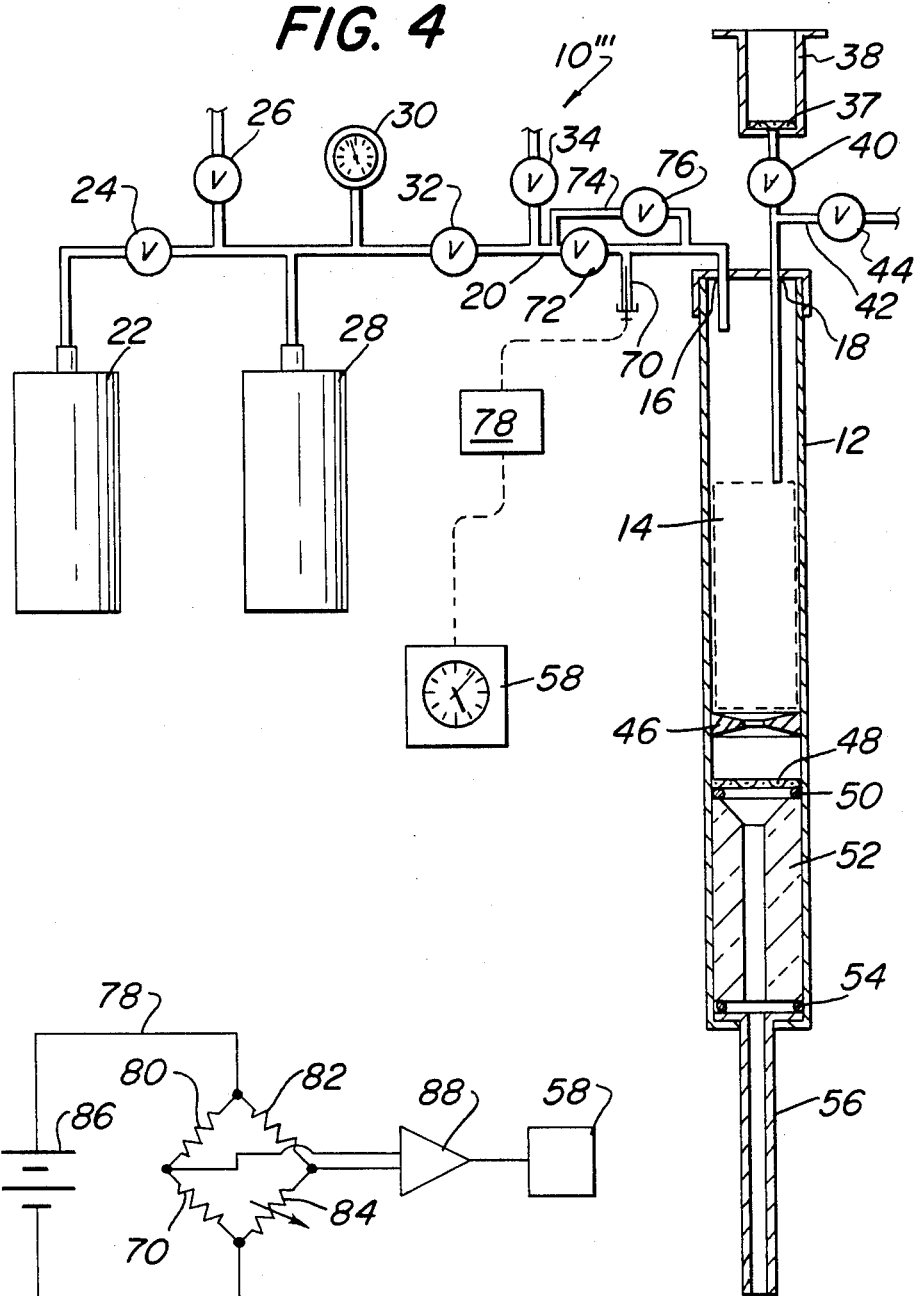
FIG. 4 is a schematic representation of a fourth embodiment.
FIG. 5 is a schematic representation of a circuit which may be used in the fourth embodiment.

Referring to FIG. 4, a fourth embodiment of the present invention 10''' is shown. The fourth embodiment is directed to a different type of gas movement sensor. The other portions of the viscometer can be the same as shown in either FIGS. 1 or 2 or 3. Like elements are denoted with like numerals.

A thermistor 70 is placed in line 20 between valve 34 and first inlet 16. Preferably, a check valve 70 is placed in line 20 between thermistor 70 and valve 34. Check valve 72 allows the flow of gas towards first inlet 16, but prevent gas movement in the opposite direction. A conduit 74 is connected to conduit 20. A first end of conduit 74 is connected to line 20 between valve 34 and check valve 72. The second end of conduit 74 is connect to conduit 20 between thermistor 70 and first inlet 16. A second check valve 76 is placed in conduit 74. Check valve 76 allows gas to move from inlet 16 towards valve 34, but prevents gas flow in the opposite direction.

Thermistor 70 is operably connected to a circuit 78. Referring to FIG. 5, the details of circuit 78 are illustrated. Of course, it is understood to those skilled in the art that alternate circuitry can be used to perform the function described hereinafter of the circuitry. The circuit 78 comprises a Wheatstone bridge which is operatively connected to an amplifier 88. Additionally, the Wheatstone bridge is connected to a power supply 86. One leg of the Wheatstone bridge comprises the thermistor 70. The amplifier 88 is operatively connected to the timer 58.

In operation, the gas flow is allowed to directly impinge upon the thermistor 70. The current supplied to the thermistor causes it to be heated to a temperature substantially above the surrounding gas. The moving gas removes the heat more efficiently from the thermistor than stagnant gas. This moving gas causes the temperature of the thermistor to decrease. As the temperature decreases, the resistance through the Wheatstone bridge is unbalanced. An amplifier notes the change in resistance and initiates the timer 58. During the period before all the sample is flushed from vessel 12, the temperature of the thermistor is allowed to stabilize. After the sample is completely passed through orifice 52, the gas again begins moving and causes a change in the temperature of the thermistor. The temperature change of the thermistor again causes the Wheatstone bridge to become unbalanced. This unbalance is picked up by the amplifier and terminates the operation of timer 58. The check valves 72 and 76 are provided to compensate for any gas moving backwards from inlet 16 due to the expansion of the oil sample in vessel 12. This check valve system increases the accuracy of this embodiment.

In operation, the viscometer is utilized to determine viscosity according to the following equation:

$$\eta = \frac{\pi g r^4 P t}{\gamma L V} - \frac{m P V}{\gamma \pi L t} \tag{1}$$

where:
$\eta$ is viscosity;
r is capillary radius;
g is acceleration due to gravity;
L is capillary length;
V is timed efflux volume;
$\rho$ is density;
P is applied pressure drop;
t is flow time;
m is kinetic energy coefficient; and $$\gamma = \frac{4v}{\pi r^3 t} \tag{2}$$

where is shear rate at the capillary wall.

The present invention is designated such that the capillary tube has a constant L and r. $\rho$ and $\eta$ are relatively constant and are well-known to and have been used heretofore by those skilled in the art. The present invention incorporates a method of achieving a repeatable efflux volume V, as defined by chamber 14, and a convenient method of measuring the efflux (lapse) time, t. Based on the design of the present invention, the above viscosity and shear rate equations can be simplified to:

$$\eta = CPT - B/t; \text{ and} \tag{3}$$

$$\delta = A/t \tag{4}$$

where:

$$C \text{ is } \frac{\pi g r^4}{\gamma L V};$$

$$B \text{ is } \frac{m P V}{\gamma \pi L};$$

and $$A \text{ is } \frac{4V}{\pi r^3},$$

The test liquid sample (generally between about 3–50 cc and preferably about 8 cc) is introduced into fill tube 38 with valves 32, 44 closed (valves 32, 34 and 64 shown in FIG. 2 are closed), and valve 34 open to the atmosphere. The sample flows down line 36 and into chamber 14. The sample remains in chamber 14 until the sample is in thermal equilibrium with the heating bath. Because the applied pressure P is nearly zero (valve 32 closed and valve 34 open), only an insignificant flow of liquid sample through capillary 52 will occur.

After the sample is brought to test temperature, it is necessary to remove any excess sample from chamber 14. Referring to FIGS. 1 and 3, valve 40 is closed. Next valve 44 on vacuum line 42 is opened. Any excess sample in chamber 14 will be drawn up line 36 and out line 40 to a trap (not shown). Referring to FIG. 2, valve 64, which is connected to a source of low pressure inert gas, is opened. The low pressure gas will force the excess sample up line 36 and into fill tube 38. Valve 40 is closed when bubbles are observed in fill tube 38. Then, valve 64 should be closed.

After any excess liquid is removed from chamber 14, valves 24, 26, 32, 34 and 40 are closed. Additionally, valve 44 of FIGS. 1 and 3 is closed and valve 64 of FIG. 2 is closed. The timer 58 is set or reset to zero. Referring to FIGS. 1 and 3, valve 32 is opened allowing pressurized gas from tank 28 into tube 12 and simultaneously a signal is sent to start timer 58. The pressurized gas forces the sample through the capillary tube 52 and then out outlet 56. After the sample has been completely forced through capillary 52, the pressurized gas exits the capillary tube 52 and outlet 56, the movement of the gas creates a "hiss" (noise). The "hiss" is heard by acoustic pick up 60, which in turn sends a signal to stop timer 58. The resulting efflux (lapse) time is then used to calculate the viscosity of the sample according to the equations noted above.

Alternatively, the embodiment shown in FIG. 3 senses pressurized gas movement in a different manner. When valve 32 is opened the pressure differential switch 66 senses the initial rush of pressurized gas into tube 12. The switch, as a result, sends a starting signal to timer 58. While the sample is being forced through the capillary tube, only minimal gas movement or pressure drop occurs. After the sample exits the capillary tube and outlet, the pressurized gas moves rapidly again, (i.e. is vented to atmosphere through outlet 56). Again the pressure differential switch senses that gas movement and sends a stopping signal to timer 58. Thus, pressure differential switch 66 both starts and stops the timer 58.

It is evident from the above disclosure that complete automation of the above viscometer can be easily accomplished by use of microprocessor technology. Furthermore, any number of the above viscometers can be joined in parallel with a common manifold for the distribution of pressurized gas. In such a case, numerous viscosity tests could be carried out in rapid succession.

The present invention may be embodied in other specific forms without departing from the spirit or essential attributes thereof and, accordingly, reference should be made to the appended claims, rather than to the foregoing specification, as indicating the scope of the invention.

We claim:

1. A viscometer for a liquid and which utilizes a pressurized gas and constant temperature bath comprises:
    a closed ended tube having a chamber;
    a first inlet in said tube for introducing said pressurized gas into said tube;
    a second inlet in said tube for introducing said liquid into said chamber and for removing excess liquid from said chamber;
    a capillary tube in communication with said chamber;
    an outlet for said liquid in communication with said capillary tube;
    a timer;
    means for starting said timer being in communication with said first inlet and operatively connected to said timer; and
    means for stopping said timer by sensing the movement of said pressurized gas after said liquid has exited said capillary tube, said stopping means being operatively connected to said timer and including a thermistor.

2. The viscometer according to claim 1 further comprising a circuit which operatively interconnects said thermistor and said timer, said circuit including a Wheatstone bridge and an amplifier, said Wheatstone bridge and said amplifier being operatively connected.

3. The viscometer according to claim 1 further comprising a plurality of check valves, said check valves being operatively associated with said first inlet.

4. The viscometer according to claim 1 wherein said starting means includes said thermistor.

5. A viscometer for a liquid and which utilizes a pressurized gas and a constant temperature bath comprises:
    a closed ended tube having a chamber;
    a first inlet in said tube for introducing said pressurized gas into said tube;
    a second inlet in said tube for introducing said liquid into said chamber and for removing excess liquid from said chamber;
    a single capillary tube in communication with said chamber;
    an outlet for said liquid in communication with said capillary tube;
    means for starting a timer being in communication with said first inlet and operatively connected to said timer; and
    means for stopping said timer by sensing the movement of said pressurized gas after said liquid has exited said capillary tube, said stopping means being operatively connected to said timer, said stopping means including a thermistor.

6. The viscometer according to claim 5 further comprising a circuit which operatively interconnects said thermistor and said timer, said circuit including a Wheatstone bridge and an amplifier, said Wheatstone bridge and said amplifier being operatively inter-connected.

7. The viscometer according to claim 5 further comprising a plurality of check valves, said check valves being operatively associated with said first inlet.

8. The viscometer according to claim 5 wherein said starting means includes said thermistor.

* * * * *